United States Patent [19]

Fitzmaurice et al.

[11] 4,101,567

[45] Jul. 18, 1978

[54] METHOD OF PREPARING CHROMIUM ALKANOATES

[75] Inventors: Colin Fitzmaurice; Norman William Fletcher Webster, both of Clwyd, Wales

[73] Assignee: Graesser Salicylates Limited, Clwyd, Wales

[21] Appl. No.: 766,976

[22] Filed: Feb. 9, 1977

[30] Foreign Application Priority Data

Feb. 13, 1976 [GB] United Kingdom ............... 5812/76

[51] Int. Cl.² ........................................... C07F 11/00
[52] U.S. Cl. ........................................ 260/438.5 R
[58] Field of Search ............................. 260/438.5 R

[56] References Cited

U.S. PATENT DOCUMENTS

| | | |
|---|---|---|
| 2,428,356 | 10/1947 | Chester et al. ............... 260/438.5 R |
| 2,615,031 | 10/1952 | Stover ......................... 260/438.5 R |
| 2,650,239 | 8/1953 | Stover ......................... 260/438.5 R |
| 2,683,156 | 7/1954 | Iler ............................. 260/438.5 R |
| 2,693,458 | 11/1954 | Olson ....................... 260/438.5 R X |

*Primary Examiner*—Helen M. S. Sneed
*Attorney, Agent, or Firm*—Oblon, Fisher, Spivak, McClelland & Maier

[57] ABSTRACT

Chromic alkanoates, especially the acetate, are prepared by reducing chromic anhydride with an alcohol in the presence of an alkanoic acid, especially acetic acid.

7 Claims, No Drawings

METHOD OF PREPARING CHROMIUM ALKANOATES

The present invention relates to chromium alkanoates, especially but not exclusively chromium acetate and provides a method of preparing said alkanoates in a novel and relatively inexpensive manner. The invention provides also a method of preparing chromium (III) salicylic complexes via said alkanoates.

Salts of chromium (III) with alkanoic (i.e. saturated aliphatic carboxylic) acids are not very well defined and their properties appear to vary according to the method of preparation. It is desired that for some applications they should have high solubility in organic solvents and it may be necessary to use particular, and often expensive, processes to obtain an acceptable form. An example of an application requiring high solubility in organic solvents is the preparation of chromium (III) salicylato complexes for use as catalysts in the condensation of an epoxide with a carboxylic acid as described in U.K. Patent Specification No. 1,277,204.

U.K. Specification No. 1,277,204 describes two types of method of preparing chromium (III) salicylato complexes both of which commence with chromium sulphate. In one type, chromic acetate monohydrate is prepared by double decomposition of chromic sulphate with barium acetate and then refluxed with a salicylic acid such as 3, 5-diisopropylsalicylic acid. In the other type a solution of a salicylic acid in aqueous ammonia or sodium bicarbonate is acidified with sulphuric acid and then added to excess aqueous chromic sulphate. These methods are not satisfactory on a commercial scale because chromium sulphate is a relatively expensive source of chromium, being about ten times as expensive as chromic anhydride, and barium acetate is not readily available. Moreover, commercially available chromium acetate is not sufficiently soluble in organic solvents to be used instead of the double decomposition product referred to above.

It has now been found that a chromic acetate which is suitable for refluxing with a salicylic acid to form a chromium (III) salicylato complex catalyst can readily be prepared from chromic anhydride (i.e. $CrO_3$; otherwise "chromium trioxide" or "chromic acid"). The method involves reduction of the anhydride with alkanol (i.e. saturated aliphatic alcohol) such as methanol or ethanol in the presence of acetic acid. The chromic acetate product can be isolated from the reaction products or can be reacted in situ with a salicylic acid to form the desired complex. It is believed that the method is of general use for preparing chromic alkanoates.

According to the present invention therefore, there is provided a method of preparing a chromic alkanoate which comprises reducing chromic anhydride with an alkanol in the presence of an alkanoic acid, especially acetic acid.

Suitably, the reduction is carried out by heating the anhydride in an aqueous alkanolic solution of the acid. Usually, the anhydride will be introduced into the reaction vessel in the form of an aqueous solution and the alkanol added slowly to said solution; the acid being added with either the anhydride or the alkanol. The reaction mixture advantageously is heated to a temperature of 60° C or above and conveniently the reduction is carried out under reflux conditions.

Preferably, the alkanol and acid have the same number of carbon atoms. The preferred acid is acetic acid, in which case the alkanol preferably is ethanol, although methanol can also be used with similar results for many purposes. In general, the acid usually will be an alkanoic acid having up to six carbon atoms and the alkanol usually will also have up to six carbon atoms. For example, the acid can be propionic acid and the alkanol can be a propanol, such as n-propanol.

The chromic alkanoate product can be isolated from the reaction products by, for example, evaporation in vacuo or reacted in situ with, for example, a higher boiling point alkanoic or alkenoic acid to form a chromic higher alkanoate or alkenoate or a salicylic acid to form a chromium (III) salicylato complex. In the latter case, reaction with a diisopropyl salicylic acid, especially 3, 5-diisopropyl salicylic acid, is preferred.

In general, the chromic alkanoates prepared by the method of this invention have a good green colour without the violet tinge shown by many chromic salts and are soluble in alcohol.

The following Examples are given by way of illustration and are not intended to limit the scope of the invention.

EXAMPLE 1

Chromic anhydride (10 g) was dissolved in a mixture of 50 ml water and 20 ml acetic acid. Methanol (15 ml) was run in slowly with stirring and the mixture was boiled under reflux until the colour had changed to deep green.

The mixture was evaporated to dryness in vacuo on a hot water bath and the green solid was dissolved in 100 ml methanol, filtered and again evaporated to dryness to yield 25 g of clear green chromic acetate which was completely soluble in methanol.

EXAMPLE 2

Chromic anhydride (15 g) was dissolved in a mixture of 75 ml water and 20 ml acetic acid. The solution was heated to 60° C on a hotwater bath and 45 ml ethanol was run in over 30 minutes. The mixture was boiled under reflux until reduction was complete and was then evaporated to dryness. The solid was dissolved in ethanol, filtered and again evaporated to dryness to yield 37 g chromic acetate apparently identical to that of Example 1.

EXAMPLE 3

Chromic anhydride (10 g) was treated with methanol and acetic acid as described in Example 1. As soon as reduction was complete, oleic acid (85 g) was added. The mixture was boiled under reflux for 2 hours and then evaporated in vacuo. The residue was taken up in methanol, filtered and evaporated again to leave 90 g chromic oleate as a green waxy solid.

EXAMPLE 4

Chromic acetate (25 g) prepared as described in Example 1 was dissolved in 100 ml methanol and treated with 67 g 3, 5-diisopropylsalicylic acid. The mixture was boiled for 30 minutes and then evaporated to dryness keeping the temperature below 85° C and finishing in vacuo. The product was dissolved in methanol, filtered and again evaporated to dryness to obtain 70 g of the chromium complex of 3, 5-diisopropylsalicylic acid as a green solid, soluble in organic solvents and showing high activity in catalysing the reaction of epoxides with aliphatic carboxylic acids.

EXAMPLE 5

Chromic anhydride (1.5 kg) was dissolved in 5 liters of water in a 10 gallon stirred glass-lined reactor. Acetic acid (2 liters) and industrial ethanol (3 liters) were added, the vessel sealed and heated to 70° C with stirring overnight. After cooling to 30° C, 3, 5-diisopropyl-salicylic acid (10 kg) was added together with a further 5 liters of alcohol. The mixture was heated to boiling and distilled at 500 mm. Hg. pressure initially followed by a reduction to about 20 mm. The product was taken into 5 liters methanol, filtered while hot and the syrupy green filtrate was spread on trays and dried in a vacuum oven to constant weight to yield 10 kg of product similar to that obtained in Example 4.

EXAMPLE 6

Chromic anhydride (15 g) was dissolved in 75 ml water and 20 ml acetic acid at 60° C, and treated with 45 ml ethanol. The mixture was boiled until no trace of yellow colour remained and then treated with 62.5 g salicylic acid. After 30 minutes the solvents were distilled off, keeping the temperature below 83° C. The final product was ground and dried in a vacuum oven at 80° C to give 67.5 g green solid, less soluble in organic solvents than the product from Examples 4 and 5 and having a somewhat lower catalytic activity.

What is claimed is:

1. A method of preparing a chromic alkanoate having up to 6 carbon atoms which comprises heating an admixture of chromic anhydride, an alkanol having up to 6 carbon atoms, an alkanoic acid having up to 6 carbon atoms and water.

2. The method of claim 1 wherein the alkanoic acid is acetic acid.

3. The method of claim 2 wherein the alkanol is selected from methanol and ethanol.

4. The method of claim 1 wherein the reduction is carried out under reflux conditions.

5. A method of preparing a chromic acetate which comprises heating an admixture of chromic anhydride, alkanol having up to 6 carbon atoms, acetic acid and water.

6. The method of claim 1 wherein the alkanol is selected from methanol and ethanol.

7. The method of claim 1 wherein the reduction is carried out under reflux conditions.

* * * * *